(12) United States Patent
Aruffo et al.

(10) Patent No.: US 6,579,271 B1
(45) Date of Patent: Jun. 17, 2003

(54) PATIENT DISCHARGE SYSTEM AND METHOD FOR SELF-CARE OF A POST-SURGERY DRAIN

(75) Inventors: Sylvia D. Aruffo, Highland Park, IL (US); Shirley P. Grey, Wauconda, IL (US); Judith Franks-Farah, Northbrook, IL (US); Carol A. Outland, Olympia Fields, IL (US)

(73) Assignee: Careguide Systems, Inc., Gurnee, IL (US)

( * ) Notice: Subject to any disclaimer, the term of this patent is extended or adjusted under 35 U.S.C. 154(b) by 171 days.

(21) Appl. No.: 09/779,796

(22) Filed: Feb. 8, 2001

Related U.S. Application Data

(60) Provisional application No. 60/181,668, filed on Feb. 11, 2000.

(51) Int. Cl.$^7$ .................................................. A61F 5/44
(52) U.S. Cl. .................. 604/355; 604/541; 206/440; 206/570
(58) Field of Search ................................. 604/541, 317, 604/327, 328, 332, 345, 355; 206/570, 440

(56) References Cited

U.S. PATENT DOCUMENTS

| | | | |
|---|---|---|---|
| 4,080,970 A | 3/1978 | Miller | |
| 4,169,550 A | 10/1979 | Williams | |
| 4,212,392 A | 7/1980 | McKenzie | |
| 4,522,302 A | 6/1985 | Paikoff | |
| 4,796,790 A * | 1/1989 | Hamilton | 224/675 |
| 5,117,981 A * | 6/1992 | Crawford et al. | 206/570 |
| 5,544,753 A | 8/1996 | Monica | |
| D380,234 S | 6/1997 | Hipple et al. | |
| 5,643,233 A | 7/1997 | Turner | |
| 5,651,777 A * | 7/1997 | Walters | 604/345 |
| 5,660,176 A | 8/1997 | Iliff | |
| 5,716,344 A * | 2/1998 | Kiel | 604/174 |
| 5,718,245 A * | 2/1998 | Horn | 128/897 |
| 5,752,234 A | 5/1998 | Withers | |
| 5,785,650 A | 7/1998 | Akasaka et al. | |
| D398,772 S | 9/1998 | Benham | |
| 5,803,249 A | 9/1998 | Harsanyi, Jr. et al. | |
| 5,803,639 A * | 9/1998 | Gusakov et al. | 401/139 |
| 5,836,497 A * | 11/1998 | Pelish | 224/677 |
| 5,848,700 A | 12/1998 | Horn | |
| 5,931,304 A | 8/1999 | Hammond | |
| 5,961,446 A | 10/1999 | Beller et al. | |
| 6,065,659 A * | 5/2000 | Faz | 224/661 |
| 6,270,485 B1 * | 8/2001 | Ekey | 604/345 |

OTHER PUBLICATIONS

J.P. Drains, Clarian Health, 1997, pp. 1 & 2.*
Drain Care After Surgery, NYU Medical Center, Mar. 2000, pp. 1 & 2.*
Care of Your Bulb Drains, Wausau Hospital, Jan. 21, 2001, pp. 1–4.*

* cited by examiner

*Primary Examiner*—Dennis Ruhl
*Assistant Examiner*—Michael G. Bogart
(74) *Attorney, Agent, or Firm*—Bell, Boyd & Lloyd LLC

(57) ABSTRACT

A patient discharge system and method for self-care of a post-surgical drain site by a patient are revealed. The system contains apparatus for at least one dressing change and includes non-latex gloves, measuring cups, gauze pads, adhesive tape remover pads, a pencil, antibacterial soap, tape, belt bags, numbered drain labels, split gauze pads with foam support bars, drainage record cards, a set of step-by-step instructions and a box having a ruler on an inside of the box top. The system includes one set of step-by-step instructions for a medical professional to instruct a patient in the use of the patient discharge system. A copy of the step-by-step instructions is included for acknowledgment by the user and retained by the medical professional for medical records.

14 Claims, 13 Drawing Sheets

FIG. 3B
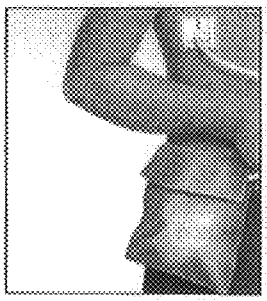
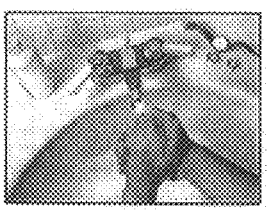
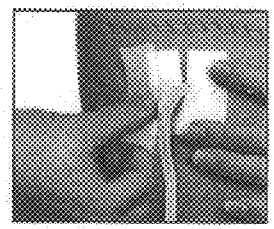
38

FIG. 4

SELF CARE DOCUMENTATION
For Use by Clinical Personnel Only

Post Surgery Drain Care     *Step-by-Step*     page 1

This sheet is a reduced-size copy of the patient's illustrated, full color instructions. The purpose of this sheet is to confirm that self care training has been carried out by the clinician and understood by the patient and/or caregiver.

Prepare for Care

A Get a clean, fresh towel. Wash your hands well with Antibacterial Soap and warm water. Dry your hands on the clean towel. Make sure you have a flat, solid surface.

B Set out one Measuring Cup for each drain. Take out a Red Plastic Bag. Open it and set it on the flat surface so it is ready for you to put in waste materials.

C Take out the Tape. Use the ruler on the inside of the box top to measure the tape. Tear the tape into two strips four inches long, for each drain and attach a small corner of each piece of tape to the edge of the counter or table near you.

D If your drains are not labeled, find the Drain Labels in the kit box and peel them off, beginning with Drain 1. Wrap one around each tube near the bulb.

The Bulb

1 Unpin Drain 1 from your clothes or take it out of the Belt Bag.

2 Put on a pair of Gloves.

3 Hold the bulb firmly with the stopper pointed over the Measuring Cup. Open the stopper. Squeeze all the contents of the bulb into the Measuring Cup.

4 Pinch the top of the tube at the exit site. Hold it tightly so you do not pull out any of the tube from your body. With the other hand, pinch and slide one finger and thumb down the tube. Squeeze and pour this last bit of fluid from the bulb into the Measuring Cup.

5 Wipe the Bulb's stopper and insertion hole with a Gauze Pad. Discard the Gauze Pad in the Red Plastic Bag.

6 Fold the bulb in half to force out all the air. Keep the bulb squeezed while you close the stopper.

Patient Name _____
Provider Name _____
Date _____

Check here when Page 1 of training is complete. ☐

Provider initials _____
Patient initials _____

44

45a

---

Post Surgery Drain Care     *continued...*     page 2

7 Place the bulb(s) and tubing inside the Belt Bag(s) around your waist. Use one bag for two bulbs.

8 Read the level of drainage on the Measuring Cup. Write it on the Drainage Record Card and label the card "Drain 1". Pour the cup contents in the toilet and put the Measuring Cup in the Red Plastic Bag.

9 Repeat Steps 1 through 8 for each additional drain you have. Keep your gloves on until the last bulb has been emptied and drainage recorded.

10 Take off the Gloves and put them in the Red Plastic Bag.

The Bandage Off with the Old

11 Wash your hands again with the Antibacterial Soap and dry them on the clean towel.

12 To make tape removal less painful, rub an Adhesive Remover Pad on the edges of the tape on your skin around the tube.

13 When the tape is loosened, remove the old gauze pad and tape by pulling the tape toward the exit site. Put them in the Red Plastic Bag.

14 Repeat Steps 12 and 13 for each exit site.

*If you are allowed to shower, now is the time. Wear your Belt Bag(s) in the shower. Let the water run over the incision(s). Gently wash around the incision. Use only the clean, fresh towel when you are drying your body. Pat, don't rub, the incision area(s). Put on as many dry Belt Bags as you need, and move the bulbs to the dry bag(s). Hang the wet Belt Bag(s) to dry.*

On with the New Bandage

*If your incision(s) is uncovered, and you would like to protect yourself from the stitches or staples "catching" on your clothes, you may tear off a piece of Microphore Tape from the roll and place it over the incision(s). This is a special, soft tape that will come off easily without pulling.*

15 Take a Slit Gauze Pad with Foam Bar. Place the pad under the drain tube so that the tube sits in the slit, resting on the foam bar for support.

16 Use the Tape you prepared to tape along one edge of the pad. Put another piece of Tape on the other side of the pad.

17 Repeat Steps 15 and 16 for each drain.

18 Twist tie the Red Plastic Bag and throw it away.

*If you need more supplies, keep the box, this Careguide™ sheet and your Belt Bags. Find the Reorder Form in the box and call the toll-free number 2 or 3 days before you run out.*

Check here when Page 2 of training is complete. ☐

Provider initials _____
Patient initials _____

We agree that the patient understands these instructions and is ready to carry out self care:

_____ Provider
Signature

_____ Patient
Signature 45c    45b

FIG. 6

| Drainage Record Card | | | |
|---|---|---|---|
| *Your doctor will tell you how often to change your dressing & record the drainage* | | | |
| DATE | TIME | AMOUNT | DAILY TOTAL / COMMENTS |
| | | cc | |
| | | cc | |
| | | cc | |
| | | cc | |
| | | cc | |
| | | cc | |
| | | cc | |
| | | cc | |
| | | cc | |
| | | cc | |
| | | cc | |

Post Surgery Drain — Step by Step — page 1

*This guide is not a substitute for your health care professionals' instructions. Review this guide with your nurse or doctor. There may be special instructions for you. Ask your doctor when you can shower and how often to change your dressings. All the medical supplies you need are in this kit. Read all the steps and use the Map to find each item before you begin. When this guide first tells you to use a thing, its name appears in RED. Keep everything in the kit until the guide tells you to use it.*

Prepare for Care

1 Find a flat, solid surface to work on, like a table or counter. If you can be in a bathroom, your self care will be easier. Get a garbage bag. Open the garbage bag and set it on the flat surface so it is ready to put in used supplies.

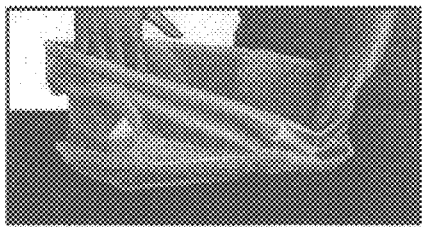

2 Get a clean, fresh towel and washcloth. Wet your hands with warm water. Pour a drop of Antibacterial Soap the size of a dime on one hand. Wash your hands well. Rinse with warm water and dry your hands on the clean towel. Set out one Measuring Cup on the flat surface.

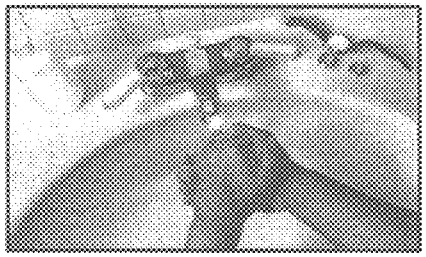

3 Take out the roll of Tape. Use the ruler on the inside of the box top to measure the tape. Tear off 2 four-inch strips. Stick one corner of each strip of Tape to the edge of the counter or table near you. Let it hang so the Tape does not stick to anything else.

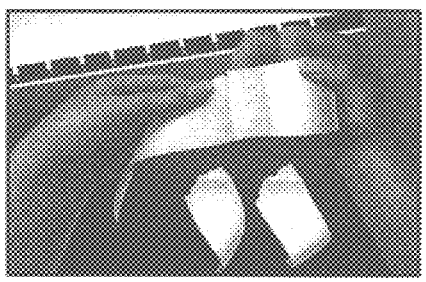

38A

4 If your drains are not labeled, find the Drain Labels in the kit. Wrap a Label around each tube, near the bulb, beginning with Drain #1.

*...continued on Page 2*

FIG. 7B

| Post Surgery Drain | Step by Step | page 2 |

The Bulb

5 Unpin Drain #1 from your clothes or take it out of the EasyWear™ Belt Bag. Lay the bulb on the flat surface.

6 Put on a pair of Gloves.

38A

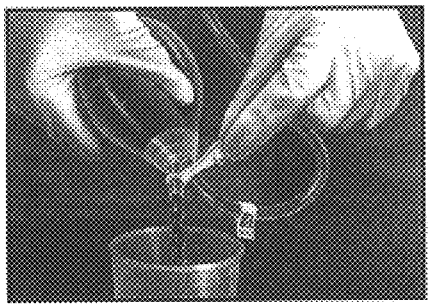

7 Hold the bulb with the insertion hole pointed over a Measuring Cup. Open the stopper. Squeeze everything from the bulb into the Cup.

8 Pinch the top of the tube at the exit site. Hold it tightly so you do not pull out any of the tube from your body. With the other hand, pinch and slide one finger and thumb down the tube. Squeeze this last bit of fluid from the bulb into the Measuring Cup. Repeat if the tube is not draining.

9 Wipe the bulb's stopper and insertion hole with Gauze. Put the Gauze in the garbage bag.

10 Squeeze the bulb in half to force out all the air. Keep squeezing while you put the stopper in the insertion hole.

11 Read the level of drainage on the Measuring Cup. Write it with the Pencil on the Drainage Record Card. Write on the card "Drain #1". Empty the Cup into the toilet.

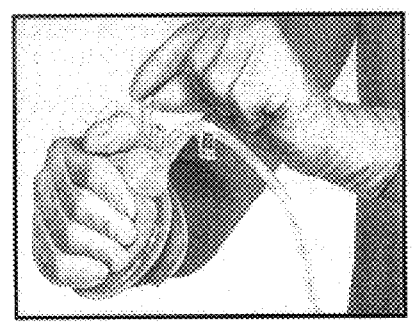

*Repeat Steps 5 through 11 for each drain. Write on the Card "Drain #2," "Drain #3," etc. Keep your Gloves on until the last bulb is empty.*

*...continued on Page 3*

FIG. 7C

| Post Surgery Drain | Step by Step | page 3 |

12. Put the Measuring Cup in the garbage bag. Take off the Gloves and put them in the garbage bag.

13. Put the bulbs inside the Belt Bags. If you have more than 2 or 3 bulbs, you can put another Belt Bag on the same Belt.

Slide the Bags around the belt until they are comfortable. Open the tabs on the belt and tuck the tubes under the tabs. Stick the tabs down to hold the tubes smoothly against your body without kinking.

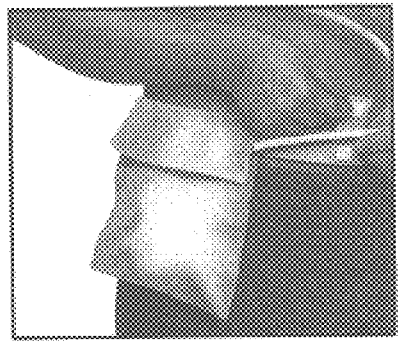

Off with the Old Dressing

14. Wash your hands again with the Antibacterial Soap and dry them on the clean towel.

15. Rub Adhesive Tape Remover on the edges of the tape on your skin around the tube. It will hurt less when the tape comes off.

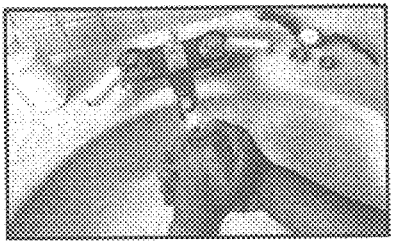

16. When the tape is loose, grab each corner and pull toward the exit site until the whole dressing comes off. Put the Adhesive Tape Remover and the old dressing in the garbage bag.

*Repeat Steps 15 and 16 for each exit site.*

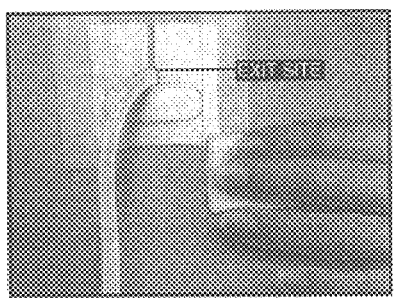

38A

Wash Your Wounds

17. If the doctor said you can shower, now is the time. Wear your Belt Bags in the shower. Let water run over the incisions. Put three drops of Antibacterial Soap on the Washcloth and make it sudsy. Gently wash around the incisions.

18. Use only the clean, fresh towel when you dry your body. Pat, don't rub, the wounds dry. Trade a dry Belt Bag from the kit for each wet Belt Bag you're wearing. Hang the wet Belt Bags to dry.

*...continued on Page 3*

FIG. 7D

| Post Surgery Drain | Step by Step | page 4 |

On with the New Dressing

*If your incisions are uncovered, and you would like to protect yourself from the stitches or staples "catching" on your clothes, tear off a piece of Tape and put it over the incisions. This is a special soft Tape that should come off easily without pulling.*

19 Take a V-Fan™ Split Pad and slip it under the tube. The tube sits in the slit, resting on the foam bar for support.

20 Use the Tape you tore earlier to tape both sides of the Split Pad.

*Repeat Steps 19 & 20 for each drain.*

21 Put any used supplies in the garbage bag, close it and put it in a waste can.

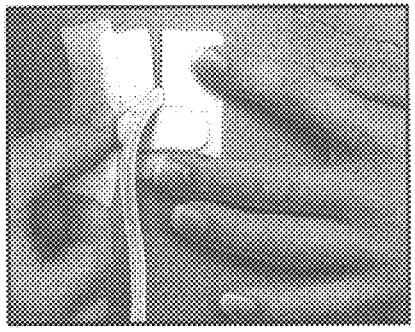

22 Wash your hands again and dry them on the clean towel. Put the Tape and any other unused supplies back in the kit for the next time.

*Call your doctor if you:*
- are hurting more and your pain medicine doesn't help
- have a temperature of 100.5°F or more
- see more redness or swelling around the incisions or exit sites
- smell a bad smell from an incision or exit site.

38A

After the doctor takes the drains out, the nurse will put a small bandage on each site. You can use an ordinary plastic bandage strip at home. Put on a new one twice a day until your skin is healed. When a drain is out, it's normal to see:
- a little redness
- a little swelling
- a little bit of clear fluid or blood on the bandage.

Special Instructions For You

Discharged Date: _____   Order Refill Date: _____

FIG. 8A

SELF CARE TEACHING DOCUMENTATION — page 1 — PATIENTS NAME

Post Surgery Drain — *Step-by-Step*

This sheet is a reduced-size copy of the patient's illustrated, full color instructions. The purpose of this sheet is to confirm that self care training has been carried out by the clinician and understood by the patient and/or caregiver.

*This guide is not a substitute for your health care professionals' instructions. Review this guide with your nurse or doctor. There may be special instructions for you. Ask your doctor when you can shower and how often to change your dressings. All the medical supplies you need are in this kit. Read all the steps and use the Map to find each item before you begin. When this guide first tells you to use a thing, its name appears in RED. Keep everything in the kit until the guide tells you to use it.*

Prepare for Care

1 Find a flat, solid surface to work on, like a table or counter. If you can be in a bathroom, your self care will be easier. Get a garbage bag. Open the garbage bag and set it on the flat surface so it is ready to put in used supplies.

2 Get a clean, fresh towel and washcloth. Wet your hands with warm water. Pour a drop of Antibacterial Soap the size of a dime on one hand. Wash your hands well. Rinse with warm water and dry your hands on the clean towel. Set out one Measuring Cup on the flat surface.

3 Take out the roll of Tape. Use the ruler on the inside of the box top to measure the tape. Tear off 2 four-inch strips. Stick one corner of each strip of Tape to the edge of the counter or table near you. Let it hang so the Tape does not stick to anything else.

4 If your drains are not labeled, find the Drain Labels in the kit. Wrap a Label around each tube, near the bulb, beginning with Drain #1.

Patient Name _____
Provider Name _____
Date _____

EDUCATION ASSESSMENT

Barriers to learning:
☐ Cognitive _____
☐ Physical _____
☐ Language _____
☐ Literacy _____
☐ Cultural _____
☐ Emotional _____
☐ Pain _____

Readiness to learn:
☐ Yes
☐ No

44A

45d

---

Post Surgery Drain — *continued...* — page 2

The Bulb

5 Unpin Drain #1 from your clothes or take it out of the EasyWear™ Belt Bag. Lay the bulb on the flat surface.

6 Put on a pair of Gloves.

7 Hold the bulb with the insertion hole pointed over a Measuring Cup. Open the stopper. Squeeze everything from the bulb into the Cup.

8 Pinch the top of the tube at the exit site. Hold it tightly so you do not pull out any of the tube from your body. With the other hand, pinch and slide one finger and thumb down the tube. Squeeze this last bit of fluid from the bulb into the Measuring Cup. Repeat if the tube is not draining.

9 Wipe the bulb's stopper and insertion hole with Gauze. Put the Gauze in the garbage bag.

10 Squeeze the bulb in half to force out all the air. Keep squeezing while you put the stopper in the insertion hole.

11 Read the level of drainage on the Measuring Cup. Write it with the Pencil on the Drainage Record Card. Write on the card "Drain #1". Empty the Cup into the toilet.

*Repeat Steps 5 through 11 for each drain. Write on the Card "Drain #2," "Drain #3," etc. Keep your Gloves on until the last bulb is empty.*

EDUCATION ASSESSMENT continued

Teaching method:
☐ Verbal
☐ Demonstration
☐ Written

Evaluation of learning:
☐ Demonstration returned
☐ Verbalizes understanding
☐ Needs assistance
☐ Unable and/or other _____

45e

45f

We agree that the patient understands these instructions and is ready to carry out self care:

Signature/Date _____ Provider

Signature/Date _____ Caregiver Patient
Circle One

FIG. 8B

SELF CARE TEACHING DOCUMENTATION

Post Surgery Drain  *continued...*  page 3

12 Put the Measuring Cup in the garbage bag. Take off the Gloves and put them in the garbage bag.

13 Put the bulbs inside the Belt Bags. If you have more than 2 or 3 bulbs, you can put another Belt Bag on the same Belt.

Slide the Bags around the belt until they are comfortable. Open the tabs on the belt and tuck the tubes under the tabs. Stick the tabs down to hold the tubes smoothly against your body without kinking.

Off with the Old Dessing

14 Wash your hands again with the Antibacterial Soap and dry them on the clean towel.

15 Rub Adhesive Tape Remover on the edges of the tape on your skin around the tube. It will hurt less when the tape comes off.

16 When the tape is loose, grab each corner and pull toward the exit site until the whole dressing comes off. Put the Adhesive Tape Remover and the old dressing in the garbage bag.

*Repeat Steps 15 and 16 for each exit site.*

Wash Your Wounds

17 If the doctor said you can shower, now is the time. Wear your Belt Bags in the shower. Let water run over the incisions. Put three drops of Antibacterial Soap on the Washcloth and make it sudsy. Gently wash around the incisions.

18 Use only the clean, fresh towel when you dry your body. Pat, don't rub, the wounds dry. Trade a dry Belt Bag from the kit for each wet Belt Bag you're wearing. Hang the wet Belt Bags to dry.

44A

---

Post Surgery Drain  *continued...*  page 2

On with the New Dressing

If your incisions are uncovered, and you would like to protect yourself from the stitches or staples "catching" on your clothes, tear off a piece of Tape and put it over the incisions. This is a special soft Tape that should come off easily without pulling.

19 Take a V-Fan™ Split Pad and slip it under the tube. The tube sits in the slit, resting on the foam bar for support.

20 Use the Tape you tore earlier to tape both sides of the Split Pad.

*Repeat Steps 19 & 20 for each drain.*

21 Put any used supplies in the garbage bag, close it and put it in a waste can.

22 Wash your hands again and dry them on the clean towel. Put the Tape and any other unused supplies back in the kit for the next time.

45g

*Call your doctor if you:*
- are hurting more and your pain medicine doesn't help
- have a temperature of 100.5°F or more
- see more redness or swelling around the incisions or exit sites
- smell a bad smell from an incision or exit site 45h After the doctor takes the drains out, the nurse will put a small bandage on each site. You can use an ordinary plastic bandage strip at home. Put on a new one twice a day until your skin is healed. When a drain is out, it's normal to see:
- a little redness
- a little swelling
- a little bit of clear fluid or blood on the bandage

Special Instructions For You

Discharged Date: _____
Order Refill Date: _____

We agree that the patient understands these instructions and is ready to carry out self care:

Signature/Date                      *Provider*

Signature/Date      *Caregiver   Patient*
                         Circle One

US 6,579,271 B1

PATIENT DISCHARGE SYSTEM AND METHOD FOR SELF-CARE OF A POST-SURGERY DRAIN

CROSS-REFERENCE TO RELATED APPLICATION

This application claims the benefit of U.S. Provisional Application No. 60/181,668, filed Feb. 11, 2000.

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

DESCRIPTION

The present invention generally relates to a patient discharge system and method for self-care of a post surgery drain, and in particular to a method and apparatus for the post-surgical drain care of an operative site by a patient or health care provider.

BACKGROUND OF THE INVENTION

Surgery may be necessary for many reasons. Surgery may offer a patient the only chance of survival in an emergency or slow down the rate of a progressive disease, such as cancer. Surgery may also be performed to improve the quality of a patient's life, as in a total hip replacement. It may be done to improve a patient cosmetically. Surgery may also be performed as a diagnostic aid, for instance, the removal of a mole or enlarged gland to test for malignancy. It may be performed to remove some obstruction or disturbance of normal bodily function, such as a gall bladder containing stones. Many other types of surgeries are preformed on a regular basis.

When a surgical operation is complete, the surgeon closes the incision. In general, the surgeon stitches the underlying tissues with sutures that are eventually absorbed by the body tissues and uses a similar type of material to sew the layer of connective tissue beneath the skin. Finally, the surgeon joins the edges of the skin together. This is done with either non-absorbable thread stitches or staples.

If the incision is in an area under a great deal of pressure, for example, a large abdominal incision, the surgeon may insert large-tension stitches to support the skin stitches, particularly if the patient has a chest problem and may strain the incision by coughing. Clips tend to mark the skin less than stitches, but generally cannot be used if the area of the incision is under great tension.

It is sometimes necessary to leave a drain in or near the incision to allow blood and other secretions to escape, either into the dressing or into a suitable container. The drain is either a tube or a piece of plastic or rubber. This is normal procedure following an operation such as a cholecystectomy.

In modern post-operative care, every effort is made to have the patient out of bed and moving around as soon as possible. After most operations, it is possible to return home before the stitches are removed. A patient is usually advised of what activities are allowed and is provided with general instructions to follow. However, there is no specific method or system which provide patients with detailed instructions and apparatus for post-surgical drain care. Thus, there is a need for a method and system for the post-surgical drain care of an operative site by a patient or health care provider in the patient's home.

SUMMARY OF THE INVENTION

The present invention provides a patient discharge system or apparatus and method for self-care of a post-surgical drain site by a patient. The system contains apparatus for at least one dressing change and comprises: (I) at least one pair of non-latex gloves; (II) at least one measuring cup; (III) at least one gauze pad; (IV) at least one adhesive tape remover pad; (V) at least one pencil; (VI) antibacterial soap; (VI) at least one piece of tape; (VII) at least one belt bag; (IX) at least one numbered drain label; (X) at least one split gauze pad with foam support bar; (XI) at least one drainage record card; (XII) at least one set of step-by-step instructions; and (XIII) a container with a ruler, where the above-named items are positioned inside the container.

In preferred embodiments of the system, the system contains sufficient apparatus for 30 dressing changes, the antibacterial soap is in liquid form, the tape is in a roll and is Micropore™ tape, the measuring cup is calibrated, and the step-by-step instructions, the numbered drain label and the drainage record card are written in English, but other languages such as Spanish are contemplated. It is also contemplated that one preferred embodiment of the system includes a contents map identifying the contents and their positions.

In a more preferred embodiment of the system, the system includes apparatus for at least 30 dressing changes as provided above and comprises: (I) 20 pairs of non-latex gloves; (II) 30 calibrated measuring cups; (III) 30 gauze pads; (IV) 30 adhesive tape remover pads; (V) a pencil; (VI) antibacterial liquid soap; (VII) a roll of Micropore™ tape; (VIII) 4 belt bags; (IX) 4 numbered drain labels; (X) 30 split gauze pads with foam support bars; (XI) 4 drainage record cards; (XII) a contents map; (XIII) a set of step-by-step instructions; and (XIV) a box having a box top with a ruler on an inside of the box top, wherein above-named items are positioned inside the box. If a waste bag is included in the system, the preferred embodiment also includes (XV) 15 plastic waste bags, otherwise waste bags may be provided by the user.

The method for self-care of a post-surgical drain site by a patient comprises changing a dressing of a post-surgical drain site with the apparatus in the system of the present invention in accordance with the detailed instructions in the system of the present invention. In a preferred embodiment, the method which is discussed in further detail below generally includes: (I) preparing for self-care; (II) draining the incision; (III) removing the old dressing; and (IV) replacing the dressing.

The present invention also includes a method for instructing or educating a user in self-care of a post-surgery drain site using the patient discharge system of the present invention. This patient education system includes a set of step-by-step instructions used by an instructor to train a user in caring for a post-surgery drain site, preferably using the system and a copy of the instructions or self-care documentation of the system.

It is therefore an object of the present invention to provide a patient discharge system and method for self-care of a post-surgery drain.

It is a further object to provide detailed instructions for post surgery self-care using the contents of a self-care a patient discharge system.

An additional object is to provide detailed instructions to be used by a medical professional in instructing users in the use of the self-care a patient discharge system.

Other objects, features and advantages of the invention will be apparent from the following detailed disclosure, taken in conjunction with the accompanying sheets of drawings, wherein like numerals refer to like parts, components and processes.

BRIEF DESCRIPTION OF THE DRAWINGS

FIGS. 3A and 3B are top plan views of one embodiment of the step-by-step instructions in English for the patient discharge system of the present invention;

FIG. 4 is a top plan view of one embodiment of a copy of the step-by-step instructions in English used by a medical professional for documenting that the users are instructed in the use of the patient discharge system of the present invention;

FIG. 6 is a top plan view of one embodiment of a drainage record card for the patient discharge system of the present invention;

FIGS. 7A, 7B, 7C and 7D are top plan views of an alternative embodiment of the step-by-step instructions in English for the patient discharge system of the present invention; and FIGS. 8A and 8B are top plan views of an alternative embodiment of a copy of the step-by-step instructions in English used by a medical professional for documenting that the users are instructed in the use of the patient discharge system of the present invention.

DETAILED DESCRIPTION OF THE INVENTION

Figure 1:
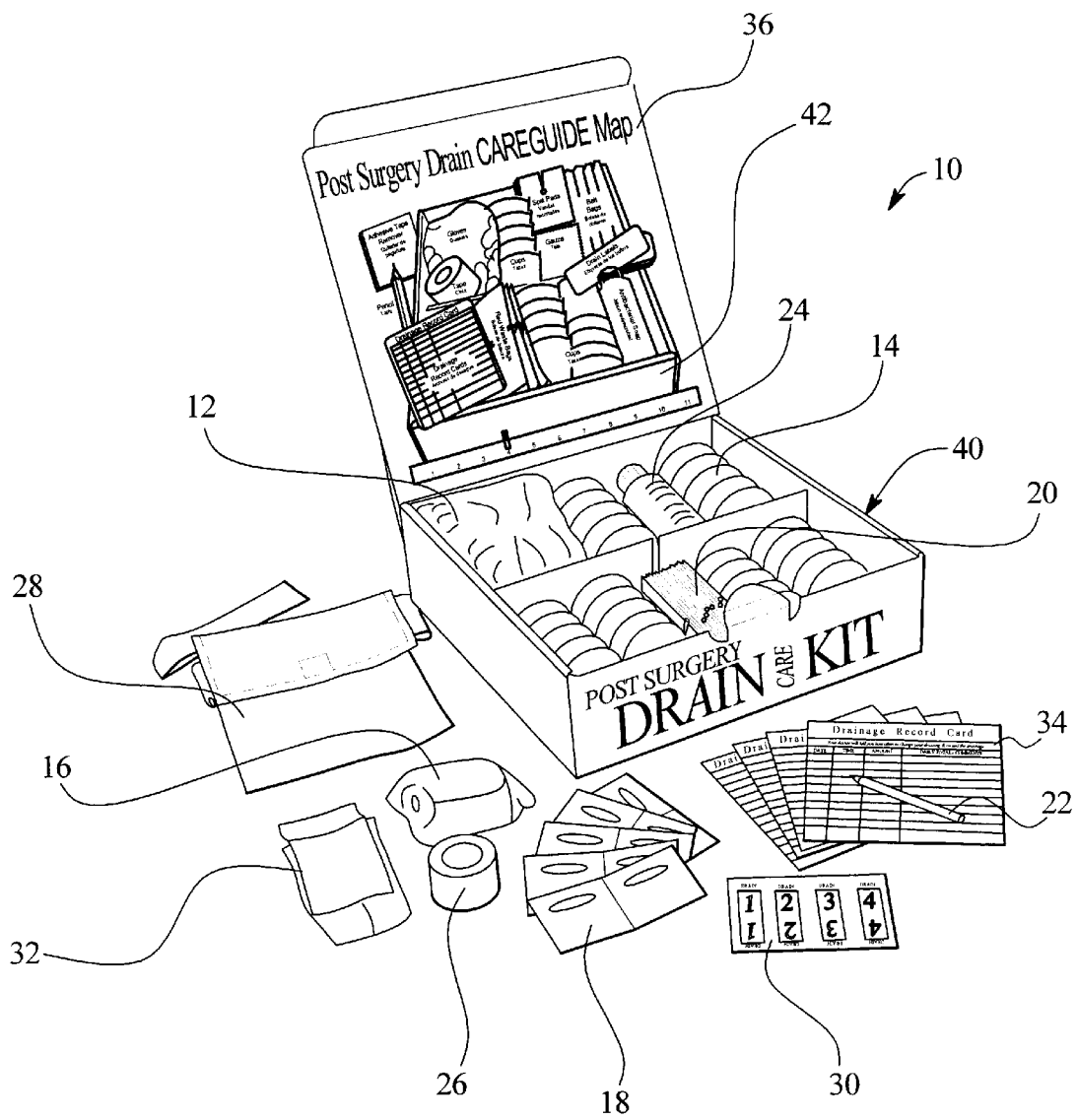
FIG. 1 is a perspective view of one embodiment of the patient discharge system of the present invention.

Referring now to the drawings, and particularly FIGS. 1, 2, 5 and 6, the present invention provides a method and or system 10 for the post-surgical drain care of an operative site by a user, whether a patient, care-giver, in-home-care provider or health-care provider. The method and system 10 provide everything that the user needs for in-home care. For brevity, the patient, care-giver, in-home-care provider and the health-care provider are referred to herein collectively as the "patient" or "user."

In general, the post-surgery drain system 10 contains at least: (I) infection prevention devices (gloves, gauze pads and soap); (II) securing devices (tape and belts); (III) measuring and labeling devices (measuring cups, a pencil, labels, record cards and a ruler); and (IV) information devices (instructions) among other items. More specifically, the post-surgery drain care system of the present invention is comprised of the following: (I) non-latex gloves 12; (II) measuring cups 14; (III) gauze pads 16; (IV) adhesive tape remover pads 18; (V) a pencil 22 or other suitable writing instrument; (VI) antibacterial soap 24; (VII) tape 26; (VIII) belt bags 28; (IX) numbered drain labels 30; (X) split gauze pads with foam support bars 32; (XI) drainage record cards 34; (XII) step-by-step instructions 38; and (XIII) a container or box 40 with a ruler 42. It is contemplated that system 10 also includes a contents map 36. The system may alternatively include waste bags 20.

Figure 2:
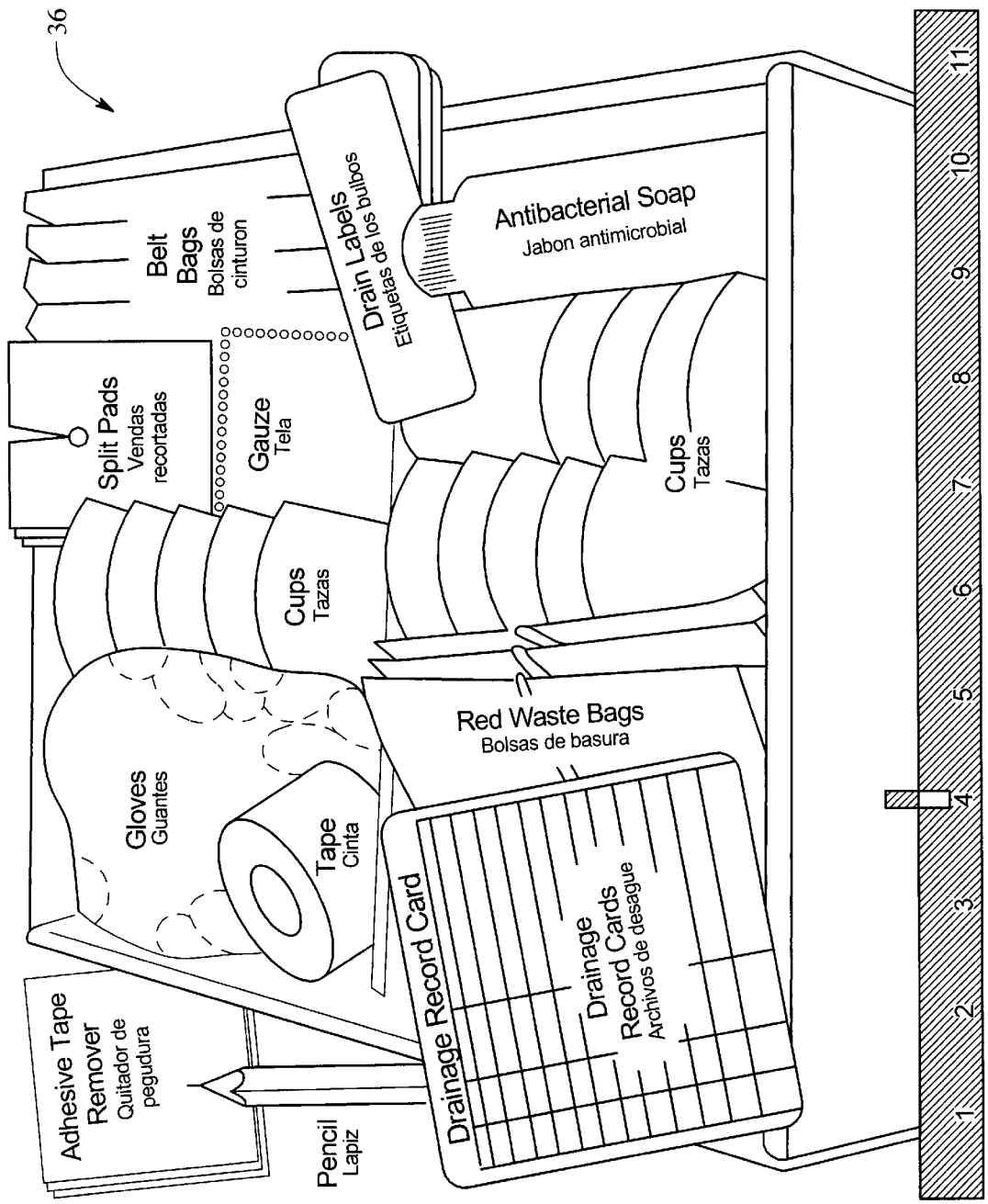
FIG. 2 is a top plan view of one embodiment of the contents map in English and Spanish for the patient discharge system of the present invention.

More specifically, the container 40 of the system contains the non-latex gloves 12, the measuring cups 14, the gauze pads 16, the adhesive tape remover pads 18, the pencil 22, the antibacterial soap 24, the tape 26, the belt bags 28, the numbered drain labels 30, the split gauze pads with foam support bars 32, the drainage record cards 34, the contents map 36 and the step-by-step instructions 38 and 38A (see FIGS. 3A and 3B or 7A, 7B, 7C and 7D, respectively) as shown in the contents map 36 (see FIGS. 1 and 2). It should be appreciated that the system 10 could also be provided to the patient in a bag, tray or any other suitable container. A box is preferred as it is strong enough to protect the contents of the system 10 and is suitable for shipping and storing. If a bag, tray or other container are used, a contents map 36 may or may not be included with system 10.

In one preferred embodiment, a clinician or other medical professional provides the system to the patient or user, although it is contemplated the user could obtain the system through other means. The system 10 includes a set of extremely detailed and specific step-by-step instructions 38 and 38A as illustrated in FIG. 3A and 3B and 7A, 7B, 7C and 7D, respectively. The instructions 38 and 38A are preferably in color for ease of use by the patient. This system also includes a black and white copy of the instructions 44 and 44A, respectively, as illustrated in FIG. 4 and FIGS. 8A and 8B. The copies do not include the illustrations of the step-by-step instructions 38 and 38A. This documentation 44 and 44A includes acknowledgement sections 45a, 45b, 45c, 45d, 45e, 45f, 45g, and 45h. It should be appreciated that the system 10 could also include an instructional video for training users in the use of the system 10.

In one of the preferred embodiments, the system 10 contains sufficient apparatus for 30 dressing changes, the antibacterial soap 24 is in liquid form, the tape 26 is in a roll and is Micropore™ tape, the measuring cup 14 is calibrated and the step-by-step instructions 38, the contents map 36 (if included), the numbered drain label 30 and the drainage record card 34 are written in English. It is also contemplated that refills for the system 10 can be provided.

In a more preferred embodiment of the system, the system 10 contains apparatus for at least 30 dressing changes and comprises: (I) 20 pairs of non-latex gloves 12; (II) 30 calibrated measuring cups 14; (III) 30 gauze pads 16; (IV) 30 adhesive tape remover pads 18; (V) a pencil 22; (VI) antibacterial liquid soap 24; (VII) a roll of Micropore™ tape 26; (VIII) 4 belt bags 28; (IX) 4 numbered drain labels 30; (X) 30 split gauze pads with foam support bars 32; (XI) 4 drainage record cards 34; (XII) a contents map 36; (XIII) a set of step-by-step instructions 38; and (XIV) a box 40 having a box top with a ruler 42 on an inside of the box top, wherein above-named items are positioned inside the box.

Using the step-by-step instructions 38 or 38A, and the contents map 36, users can easily identify when each item is required in the method and readily find it in the container 40. It should be appreciated that the items and step-by-step instructions could be color coded and/or use icons making identifying each item even easier. For example, the gauze pads could be identified by a band aid icon and blue coloring corresponding to a band aid icon and blue coloring in the step-by-step instructions.

The method for self-care of a post-surgical drain site by a patient comprises changing a dressing of a post-surgical drain site using the system 10 in accordance with the detailed instructions 38 or 38A. In a preferred embodiment, the method generally includes: (I) preparing for self-care; (II) draining the incision; (III) removing the old dressing; and (IV) replacing the dressing.

Preparing For Self-care (Step I)

Figure 3A:
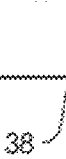
Figure 5:
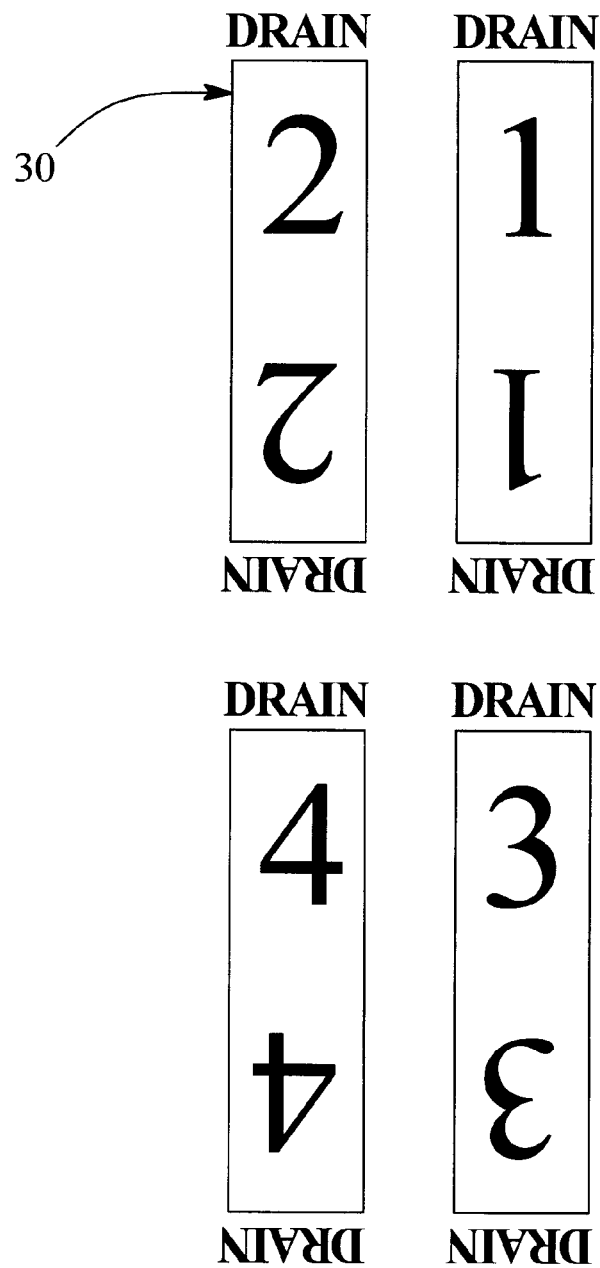
FIG. 5 is a top plan view of one embodiment of the numbered drain labels for the patient discharge system of the present invention.

The first step of one embodiment of the method of the present invention, as illustrated in FIGS. 3A and 3B, includes preparing for self-care. Preparing for self-care includes: (I) obtaining a clean, fresh towel; (II) (a) washing using antibacterial soap 24 and warm water; and (b) using the clean towel for drying; (III) finding a flat, solid surface; (IV) setting out a measuring cup 14 for each drain; (V) preparing a waste bag 20 which includes: (a) obtaining a waste bag 20 either from system 10 or some other source; and (b) opening the waste bag 20; (VI) setting the waste bag 20 on the flat surface so it is ready for waste materials; (VII) preparing the tape which includes: (a) taking the tape 26 out of the container 40; (b) measuring the tape 26 using the ruler 42; (c) tearing the tape 26 into two strips approximately four inches long for each drain; and (d) attaching a small corner of each piece of tape 26 to the edge of the counter, table or other surface; and (VII) labeling each drain using the numbered drain labels 30 (see FIG. 5) which includes: (a) peeling the labels 30 off the backing starting with the Drain 1 label; and (b) wrapping one label around each tube near the bulb. It should be appreciated that this process can be skipped if the drains are labeled.

An alternative embodiment of the first step of the method of the present invention, as illustrated in FIGS. 7A, 7B, 7C and 7D includes preparing for self-care. Preparing for self-care includes: (I) finding a flat solid surface to work on such as a table or counter; (II) finding a garbage bag and setting it up to put in used apparatus; (III) obtaining a clean, fresh towel; (IV) (a) washing using antibacterial soap 24 and warm water; and (b) using the clean towel for drying; (V) setting out a measuring cup 14; (VI) preparing the tape which includes: (a) taking the tape 26 out of the container 40; (b) measuring the tape 26 using the ruler 42; (c) tearing the tape 26 into two strips approximately four inches long for each drain; and (d) attaching a small corner of each piece of tape 26 to the edge of the counter, table or other surface; and (VII) labeling each drain using the numbered drain labels 30 which includes: (a) peeling the labels 30 off the backing starting with the Drain 1 label; and (b) wrapping one label around each tube near the bulb. It should be appreciated that this process can be skipped if the drains are labeled.

Draining the Incision (Step II)

The second step of method of the present invention includes draining the incision as provided in FIGS. 3A and 3B or FIGS. 7A, 7B, 7C and 7D. Draining the incision includes: (I) unpinning or removing Drain 1 from the belt bag 28; (II) putting on a pair of gloves 12; (III) holding the bulb firmly and pointing the stopper over the measuring cup 14; (IV) opening the stopper and squeezing all of the contents of the bulb into the measuring cup 14; (V) pinching the top of the tube at the exit site while holding it so that is does not pull loose or out; (VI) pinching the tube while sliding downward, squeezing and pouring the last bit of fluid from the bulb into the measuring cup 14; (VII) wiping the bulb's stopper and insertion hole with a gauze pad 16; (VII) discarding the gauze pad 16 in the waste bag 20; (IX) folding the bulb in half to force out all the air; (X) placing the bulb(s) and tubing inside the belt bags(s) 28 using one belt bag 28 for two bulbs; (XI) reading the level of drainage on the measuring cup 14; (XII) recording the drainage including: (a) writing the amount on the drainage record card 34 (see FIG. 6); and (b) labeling the card "Drain 1"; (XIII) disposing of the drainage, preferably in the toilet; (XIV) placing the used measuring cup 14 in the waste bag 20; (XV) repeating the above process for each additional drain, while keeping the gloves 12 on until the last bulb has been emptied and drainage recorded; and (XVI) disposing of the gloves including (a) taking off the gloves 12; and (b) placing the gloves in the waste bag 20.

Removing the Old Dressing (Step III)

The third step of the method of the present invention includes removing the old dressing as illustrated in FIGS. 3A and 3B and FIGS. 7A, 7B, 7C and 7D. Removing the old dressing includes: (I) washing which includes (a) using the antibacterial soap 24; (b) drying using the clean towel; (II) rubbing an adhesive remover pad 18 on the edges of the tape 26 and skin around the tube assisting in removal of the tape 26 (i.e., make removing the tape less painful); (III) removing the old gauze pad 16 and tape 26 by pulling the tape toward the exit site when the tape 26 is loosened; (IV) disposing of the tape 26 and old gauze pad 16, preferably in the waste bag 20; and (V) repeating the process for each exit site. If the patient is allowed to shower, this third step further includes: (VI) showering while wearing the belt bag(s) 28 in the shower, which includes: (a) letting the water run over the incision(s); (b) gently washing around the incision; (b) drying using only the clean, fresh towel while patting, not rubbing, the incision area(s); (c) putting on as many dry belt bags 28 as needed; (d) moving the bulbs to the dry bag(s) 28; and (e) hanging the wet belt bag(s) 28 to dry.

Replacing the Dressing (Step IV)

The fourth step of method of the present invention includes replacing the dressing as illustrated in FIGS. 3A and 3B and FIGS. 7A, 7B, 7C and 7D. Replacing the dressing includes (I) protecting the uncovered incision from catching or snagging, which includes: (a) tearing off a piece of Micropore™ Tape 26 from the roll; and (b) placing it over the incision(s); (II) taking a slit gauze pad with foam support bar 32 out of the box 40; (III) positioning the drain tube, which includes: (a) placing the pad 32 under the drain tube so that the tube sits in the slit; and (b) resting the drain tube on the foam bar for support; (IV) taping the slot gauze pad with foam support bar 32 in place, which includes: (a) using the tape 26 prepared previously (see Step I above) to tape along one edge of the pad 32; and (b) placing another piece of tape 26 on the other side of the pad; (V) repeating this process for each of the drains; and (VI) twisting the tie around the waste bag 20 and throwing it away.

Yet another embodiment of the present invention includes teaching or instructing the patient or user in the use of the system 10. The system includes a copy of the set of extremely detailed and specific step-by-step instructions 44 or 44A, as illustrated in FIGS. 4 and FIGS. 8A and 8B and discussed previously, for a medical care professional or clinician. The medical care professional uses the copy of the instructions to document the instructions provided to the patient or user, familiarizing the patient or user with the method and system 10. The instructions enables the medical care professional to ensure that the training is complete, providing a plurality of places 45a, 45b, 45c, 45d, 45e, 45f, 45g, and 45h for the patient or user to indicate they have received and understand the instructions. These instructions 44 or 44A are maintained by the clinician or medical provider as part of the clinical record, where they may by used for accreditation and/or legal purposes.

It will be appreciated that the system 10 may contain sufficient apparatus for one or more dressing changes, for example, apparatus for 1, 5, 10, 15, 20, 25, 30, 40 or 50 dressing changes. Further, it should be appreciated that refills for system 10 may be provided. For example, additional gauze pads 16 or tape 26 may be provided as required by the user. The antibacterial soap 24 may be in liquid or bar form. The tape is preferably a roll of Micropore™ tape 26. The measuring cups 14 are preferably calibrated. The step-by-step instructions 38 or 38A and 44 or 44A, the contents map 36, the numbered drain labels 30 and the drainage record cards 34 may be written in any language, including English, Spanish, French, etc.

The present invention further contemplates a method for instructing or educating users in post-surgery drain site care in accordance with the step-by-step instructions provided in the patient discharge system of the present invention. More specifically, the system includes self-care documentation 38, 38A, 44 and 44A. An instructor such as a doctor, nurse, clinician, other medical professional or any individual trained to educate users in caring for a post-surgery drain site uses the step-by-step instructions to instruct the user to care for the post-surgery drain site, preferably using the system of the present invention. The instructor takes the user through the method of the present invention and may even demonstrate specific procedures using specific items of the system of the present invention. It should also be appreciated that the system, including the step-by-step instructions of the present invention could be employed by the patient for self-education.

Federal, state and local regulatory agencies require full documentation of training provided by the medical care professional. The medical care professional uses the documentation described above to document the instructions provided to the patient or user, familiarizing the patient or user with the method and system of the present invention. The copy of the instructions enable the medical care professional to ensure that the training is complete, providing acknowledgment sections 44A through 44H for the patient or user to indicate (i.e., initial or signed) that they have received and understand the instructions. This documentation is maintained by the clinician or medical provider as part of the clinical record, were they may be used for accreditation and/or legal purposes.

While the invention has been described in connection with what is presently considered to be the most practical and preferred embodiments, it is to be understood that the invention is not limited to the disclosed embodiments, but on the contrary is intended to cover various modifications and equivalent arrangements included within the spirit and scope of the appended claims. Thus, it is to be understood that variations in the present invention can be made without departing from the novel aspects of this invention as defined in the claims.

The invention is hereby claimed as follows:

1. A system for care of a post-surgical drain site by a patient, said system comprising:
    (a) at least one pair of gloves;
    (b) at least one measuring cup;
    (c) at least one gauze pad;
    (d) at least one tape remover;
    (e) antibacterial soap;
    (f) at least one securing device;
    (g) at least one belt bag;
    (h) at least one drain label;
    (i) at least one split gauze pad with foam support bar;
    (j) at least one drainage record card;
    (k) at least one set of step-by-step instructions; and
    (l) at least one container for holding apparatus (a) to (k).

2. The system of claim 1, wherein the container is a box and wherein items (a) through (k) are positioned inside the box according to a contents map.

3. The system of claim 2, wherein said system contains apparatus for a plurality of self-care procedures.

4. The system of claim 3, wherein the antibacterial soap is in liquid form.

5. The system of claim 3, which includes at least one waste bag.

6. The system of claim 3, further including a tape within a roll.

7. The system of claim 3, wherein the measuring cup is calibrated.

8. The system of claim 3, which includes at least one set of clinician step-by-step instructions for documenting instructions provided to the patient in the use of the system.

9. A method for self-care of a post-surgical drain site by a patient comprising caring for a post-surgical drain site with the system of claim 1.

10. The method of claim 9, which includes caring for the post-surgical drain site by following said step-by-step instructions.

11. The method of claim 9, which includes preparing for self-care of a post-surgical drain.

12. The method of claim 9, which includes draining the post-surgical drain site.

13. A system for at least 30 self-care procedures for a post-surgical drain site by a patient, said system comprising:
    (a) 20 pairs of gloves;
    (b) 30 calibrated measuring cups;
    (c) 30 gauze pads;
    (d) 30 adhesive tape remover pads;
    (e) a writing instrument;
    (f) antibacterial liquid soap;
    (g) a roll of tape;
    (h) 4 belt bags;
    (i) 4 numbered drain labels;
    (j) 30 split gauze pads with foam support bars;
    (k) 4 drainage record cards;
    (l) a set of step-by-step instructions; and
    (m) a box adapted to hold apparatus (a) through (l).

14. The system of claim 13, which includes at least one set of clinician step-by-step instructions for documenting instructions provided to the patient in the use of the system.

* * * * *

UNITED STATES PATENT AND TRADEMARK OFFICE
CERTIFICATE OF CORRECTION

PATENT NO. : 6,579,271 B1  Page 1 of 1
DATED : June 17, 2003
INVENTOR(S) : Sylvia D. Aruffo et al.

It is certified that error appears in the above-identified patent and that said Letters Patent is hereby corrected as shown below:

Column 2,
Line 13, (2$^{nd}$ occurrence) change "VI" to -- VII --.
Line 14, change "VII" to -- VIII --.
Line 40, change "wherein above-named" to -- wherein the above-named --.
Line 43, change "bags otherwise" to -- bags; otherwise, --.
Lines 66-67, change "a patient" to -- patient --.

Column 3,
Line 3, change "a patient" to -- patient --.

Column 5,
Line 23, change "(VII) labeling" to -- (VIII) labeling --.
Lines 62-63, change "(VII) discarding" to -- (VIII) discarding --.

Column 6,
Line 27, change "(b)" to -- (c) --.
Line 29, change "(c)" to -- (d) --.
Line 30, change "(d)" to -- (e) --.
Line 31, change "(e)" to -- (f) --.
Line 34, change "of method" to -- of the method --.
Line 60, change "enables" to -- enable --.
Line 66, change "by" to -- be --.

Column 7,
Line 44, change "were" to -- where --.

Signed and Sealed this

Twentieth Day of January, 2004

JON W. DUDAS
*Acting Director of the United States Patent and Trademark Office*